United States Patent
Davey (10) Patent No.: US 7,294,296 B2
(45) Date of Patent: Nov. 13, 2007

(54) VALVED INTRODUCER SHEATH AND RELATED METHODS

(75) Inventor: Christopher T. Davey, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 478 days.

(21) Appl. No.: 10/929,302

(22) Filed: Aug. 30, 2004

(65) Prior Publication Data
US 2005/0027257 A1 Feb. 3, 2005

Related U.S. Application Data (62) Division of application No. 09/556,102, filed on Apr. 21, 2000, now Pat. No. 6,808,509.

(60) Provisional application No. 60/130,541, filed on Apr. 22, 1999.

(51) Int. Cl.
*B29C 44/06* (2006.01)
(52) U.S. Cl. ............... 264/46.6; 264/154; 264/267
(58) Field of Classification Search ............ 264/46.6, 264/267, 268, 154; 604/167.04, 167.05
See application file for complete search history.

(56) References Cited

U.S. PATENT DOCUMENTS

| 4,751,947 A | * | 6/1988 | Landers | 141/1 |
| 5,104,389 A | * | 4/1992 | Deem et al. | 604/264 |
| 5,556,387 A | * | 9/1996 | Mollenauer et al. | 604/249 |
| 5,755,693 A | * | 5/1998 | Walker et al. | 604/160 |

* cited by examiner

*Primary Examiner*—Allan R. Kuhns
(74) *Attorney, Agent, or Firm*—Fay Kaplun & Marcin, LLP

(57) ABSTRACT

A valved introducer sheath is used to facilitate the insertion of a flexible medical device into a body. The elongated valve of the valved introducer sheath is constructed of a foam material that is injected into the sheath and sliced longitudinally to create one or more self-sealing slits through which flexible medical devices can be passed. As a medial device is passed through the self-sealing slit(s) at a proximal end, the self-sealing slits seal around the medical device before opening at a distal end. The elongated valve is also affixed to at least some of the inner surface of the sheath. The valve will tear into halves along at least one of the self-sealing slits when the sheath is peeled.

10 Claims, 7 Drawing Sheets

VALVED INTRODUCER SHEATH AND RELATED METHODS

CROSS REFERENCE TO RELATED CASE

This application is a Division of prior U.S. patent application Ser. No. 09/556,102 filed Apr. 21, 2000, now U.S. Pat. No. 6,808,509 entitled "VALVED INTRODUCER SHEATH AND RELATED METHODS" which claims priority to and the benefit of U.S. Provisional Application Serial No. 60/130,541 filed Apr. 22, 1999. The entire disclosure of these prior applications is considered as being part of the disclosure of the accompanying application and hereby expressly incorporated by reference herein.

TECHNICAL FIELD

This relates to a medical device used to aid the introduction of another medical device into the body, and to methods of making and using such an introduction-aiding device. More particularly, this relates to an introducer system useful in the placement of a catheter into the body, and to methods of making and using such a system.

BACKGROUND INFORMATION

In general, sheaths used to facilitate the insertion of devices, such as catheters, into the body are known. A catheter (or other medical device) can be inserted, with the use of a known sheath, percutaneously into the body, and the sheath can be torn off after insertion of the catheter. Tearable sheaths generally are referred to as peelable sheaths. There are also non-peelable sheaths. Peelable sheaths generally are used to introduce devices which are left in (or at least partially within) the patient after the procedure is completed, and a dialysis catheter is one example of a medical device that is left within the patient after a placement procedure. Non-peelable sheaths generally are used when the introduced device is removed at the end of the procedure.

Known peelable sheaths generally include a hub located at the proximal end of the sheath, and the hub can be manually grasped and pulled apart to permit the longitudinal severance of the hub and the sheath thereby to allow the removal of the sheath and hub from about the catheter extending therethrough and from the body. Such known peelable sheath/hub combinations typically are provided with a dilator, and the whole package generally is referred to as a peelable introducer system or simply an introducer system. Introducer systems with non-peelable sheaths also are known.

Some introducer systems, with the dilator inserted into and through the peelable sheath/hub, are designed to be advanced over a guide wire that is indwelling in a vein, artery, or other body cavity of a medical patient. In general, whether or not used with a guide wire, an introducer system is a medical device for insertion into the body (e.g., into a vein, such as the jugular vein, of a patient). In one possible use, the introducer system is placed into a patient's vein in order to allow a flexible catheter to be placed later within the same vein through the sheath/hub of the introducer system after the dilator component of the introducer system is removed from the sheath/hub component.

Various types of peelable and non-peelable sheaths and introducer systems are available from Boston Scientific Corporation (Natick, Mass.) and other companies. Boston Scientific Corporation provides certain peelable sheaths and introducer systems in its commercially-available Vaxcel PICC kits.

Some known introducer systems include a valve to provide a seal around the catheter introduced through the sheath.

In general, known valved peelable introducer systems include two basic components: (1) a peel-away sheath/hub, where the hub is fixed to the proximal end of the sheath; and (2) a more rigid dilator that is sized to slide and fit snugly into a lumen extending through the sheath/hub. The hub generally is provided either as two identical separate halves (split along the length of the hub) or as a single unit with scoring or perforations on both sides along its length to allow the sheath hub to be broken into two identical separate halves. The dilator has a proximal hub portion and a longer tubular portion, and a passage typically extends through the dilator such that the dilator can be passed over a guide wire, for example. The tubular portion of the dilator is designed to extend through the sheath and the hub, and the proximal hub of the dilator can lock (e.g., via a luer lock) onto the hub of the sheath. A valve is incorporated into the hub of the sheath, and the dilator passes through this valve when the dilator is inserted into and through the sheath/hub. The valve typically is a thin, disk-like membrane.

In a typical use, a known valved introducer system (with the dilator inserted into the sheath/hub and through the valve) is inserted into a patient's vein (usually over a guide wire that is already in the vein) up to the sheath's hub such that most or all of the sheath is within the patient's vein and most of the dilator also is within the patient's vein, while the hubs of the sheath and the dilator are outside of the patient's body. The dilator is then removed from the sheath and from the patient's body. With the dilator removed, the valve is supposed to close and prevent air from entering the vein, which generally would happen if the passage through the sheath was open, because of negative pressure in the vein. The catheter (or other medical device) is now supposed to be inserted through the hub, valve, and sheath and thus into the patient's vein.

Known valved introducer systems generally have at least two issues. First, the valve may be too rigid to allow flexible devices, such as flexible catheters, to be inserted therethrough. Many catheters do not have enough column strength or rigidity to be passed through a tight valve. Second, if the valve is sufficiently flexible to allow a flexible catheter to be inserted therethrough, the valve may become malpositioned after the dilator is removed. That is, the valve may not close properly after removal of the dilator, and thus the danger of air entering the body or blood leaving the body is not avoided by use of the valve.

SUMMARY OF THE INVENTION

In general, the invention relates to a valved introducer sheath and associated methods of making and using such a sheath. The sheath can include a body portion and a proximal hub portion, with a passageway extending through the entire length of the sheath. The passageway is sized to receive a dilator that generally is more rigid than the body portion of the sheath. The elongated body portion of the sheath can be generally circular in cross-section and can have a first section that has a larger diameter than a second section. The body portion of the sheath could have one or more non-circular cross-sectional shapes. Along and within at least a portion of the passageway of the sheath, an elongated valve extends longitudinally. This elongated valve can be formed of foam or other compliant material that will allow the dilator to pass therethrough and that will form a seal therearound, and that will also close and form a reliable seal after the dilator is removed. The elongated valve of the invention also will allow a device more flexible than the dilator (e.g., a catheter) to be passed therethrough, and it will form a seal around such a device and then close and seal after the device is removed.

The valved introducer sheath of the invention can be "peelable" in that the body portion, hub, and valve can be manually broken apart, split, and peeled from around the device that extends therethrough. Once peeled from around the inserted device and removed from the body of the patient, the two halves of the now-split valved introducer sheath typically are discarded. In an alternative embodiment, the valved introducer sheath of the invention is not designed to be peelable.

The elongated valve provides better performance than existing valves in terms of at least the valved introducer sheath's ability to prevent reliably the influx of air (and/or the outflow of blood) as the dilator is being removed and after it is removed. The elongated valve of the invention can be opened and closed (by, for example, inserting and removing a dilator or other more flexible device such as a catheter) repeatedly without losing its ability to provide a reliable seal. Also, when the dilator is removed from the valve, and no medical device is present in the valve, the valve material is in an unstressed state.

In one aspect, the invention involves a method of producing a valved sheath. The sheath comprises a proximal hub portion, an elongated body portion extending distally from the proximal hub portion, and a passageway extending through the proximal hub and elongated body portions. A foam material is injected into at least some of the passageway. In the foam material, one or more self-sealing slits are formed. The foam material and the one or more slits serve as a valve in the passageway of the sheath.

Embodiments according to this aspect of the invention can include the following features. The foam material can be injected such that the length of the foam material within the passageway is greater than the width of the foam material at any point within the passageway. The foam material can be a closed cell foam. The foam material can be affixed to at least some of an inner surface of the sheath. The self-sealing slits can be formed such that none of them extends in width to an inner surface of the sheath. The self-sealing slits substantially prevent the flow of gas into the passageway of the sheath. Scorings or lines can extend at least some of the length, and on opposite sides, of the sheath, such that the sheath is separable along the scorings or lines. The proximal hub portion can comprise a pair of wings that extend substantially perpendicular to the elongated body portion of the sheath.

In another aspect, the invention relates to apparatus for facilitating the insertion of a flexible medical device into a body. The apparatus comprises a sheath and a valve. The sheath comprises a proximal hub portion, an elongated body portion which extends distally from the proximal hub portion, and a passageway which extends through the proximal hub and elongated body portions. At least some of the elongated body portion is capable of being placed into the body. The passageway is defined by an inner surface of the sheath. The valve comprises a foam material which fills at least some of the length of the passageway, and one or more self-sealing slits are in the foam material. The length of the foam material within the passageway is greater than the width of the foam material at any point within the passageway. None of the slits extends in width to the inner surface of the sheath, and the slits are capable of allowing the flexible medical device to pass therethrough and sealing around the device.

Embodiments according to this other aspect of the invention can include the following features. The foam material can include a proximal section and a distal section, where the one or more slits in the distal section remain sealed as the flexible medical device is introduced first into the one or more slits in the proximal section. The foam material can define a depression in the proximal section, and the depression can have a conical shape for receiving the flexible medical device. The foam material can be a closed cell foam. The foam material can be affixed to at least some of an inner surface of the sheath. A pair of scorings or lines can extend at least some of the length, and on opposite sides, of the sheath, such that at least the sheath is separable along the lines. The valve, too, can be separable with the sheath and can be split into two halves along one of the self-sealing slits. The elongated body portion can comprise at least a first section and a second section, where a first cross-sectional area of the first section is greater than a second cross-sectional area of the second section. The elongated body portion also can comprise a shoulder disposed within the passageway and between the first and second sections. The proximal hub portion can comprise a pair of wings which extend substantially perpendicular to the elongated body portion of the sheath.

In yet another aspect, the invention involves apparatus for facilitating the insertion of a flexible medical device into a body. The apparatus comprises a sheath and a valve. The sheath comprises a proximal hub portion, an elongated body portion which extends distally from the proximal hub portion. At least some of the elongated body portion is capable of being placed into the body. The passageway is defined by an inner surface of the sheath. The valve comprises a foam material which fills at least some of the length of the passageway, and one or more self-sealing slits are in the foam material. The length of the foam material within the passageway is greater than the width of the foam material at any point within the passageway. The foam material is affixed to a portion of the inner surface of the sheath, and the slits are capable of allowing the flexible medical device to pass therethrough and sealing around the device.

Embodiments according to this aspect of the invention can include the following features. The foam material can include a proximal section and a distal section, where the one or more slits in the distal section remain sealed as the flexible medical device is introduced first into the one or more slits in the proximal section. The foam material can define a depression in the proximal section, and the depression can have a conical shape for receiving the flexible medical device. The foam material can be a closed cell foam. A pair of scorings or lines can extend at least some of the length, and on opposite sides, of the sheath, such that at least the sheath is separable along the lines. The valve, too, can be separable with the sheath and can be split into two halves along one of the self-sealing slits. Each of the halves of the valve remain affixed to the respective halves of the sheath when the sheath and valve are separated. None of the one or more self-sealing slits in the foam material extend in width to the inner surface of the sheath. The proximal hub portion can comprise a pair of wings which extend substantially perpendicular to the elongated body portion of the sheath.

In still another aspect, the invention relates to apparatus for facilitating the insertion of a flexible medical device into a body. The apparatus comprises a sheath and a valve. The sheath comprises a proximal hub portion, an elongated body portion which extends distally from the proximal hub portion, and a passageway extending through the proximal hub and elongated body portions. The valve comprises an injected foam material which fills at least some of the length of the passageway, and one or more self-sealing slits are in the foam material. The length of the foam material within the passageway is greater than the width of the foam material at any point within the passageway.

Embodiments according to this aspect of the invention include the following features. The foam material can include a proximal section and a distal section, where the one or more slits in the distal section remain sealed as the flexible medical device is introduced first into the one or more slits in the proximal section. The foam material can define a depression in the proximal section, and the depression can have a conical shape for receiving the flexible medical device. The foam material can be a closed cell foam. In one embodiment, none of the one or more self-sealing slits extends in width to an inner surface of the sheath that defines the passageway. The one or more self-sealing slits substantially prevent the flow of gas into the passageway of the sheath. A pair of scorings or lines can extend at least some of the length, and on opposite sides, of the sheath, such that at least the sheath is separable along the lines. The valve, too, can be separable with the sheath. The proximal hub portion can comprise a pair of wings which extend substantially perpendicular to the elongated body portion of the sheath.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 9:
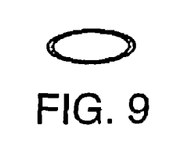
FIG. 9 shows a possible non-circular cross-sectional shape of a portion of the sheath of FIG. 1.
Figure 10:
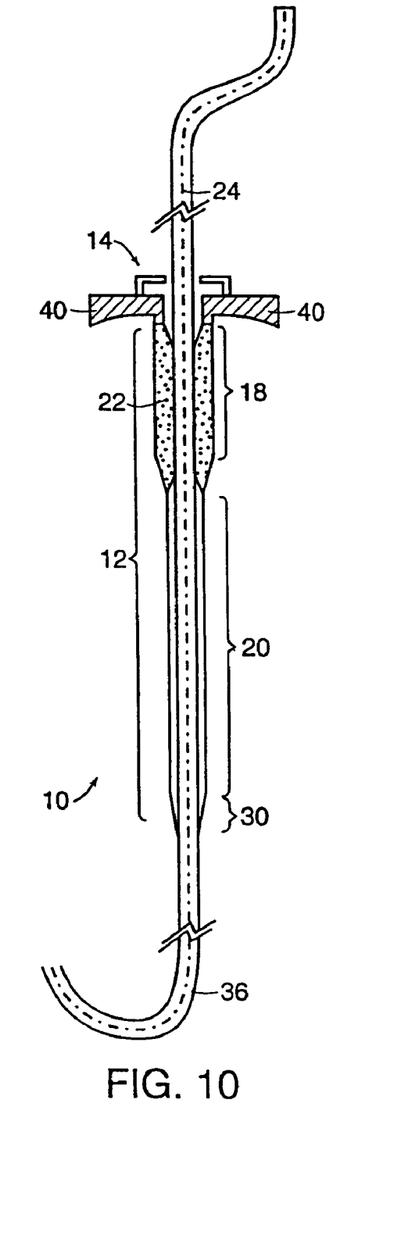
FIG. 10 is a partial sectional view of the valved introducer sheath of FIG. 1, with a flexible catheter inserted into the sheath and thus with the valve of the sheath open.
Figure 11:
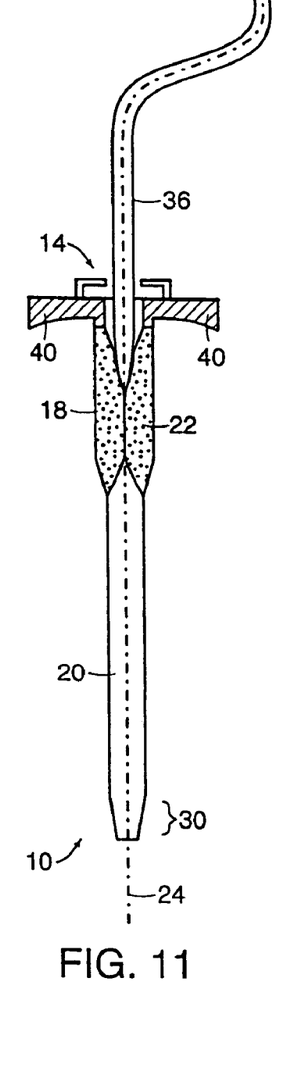
FIG. 11 is a partial sectional view of the sheath of FIG. 10, with the catheter of FIG. 10 partially removed from the sheath and thus with the valve of the sheath closed along a distal part of its length.
Figure 12:
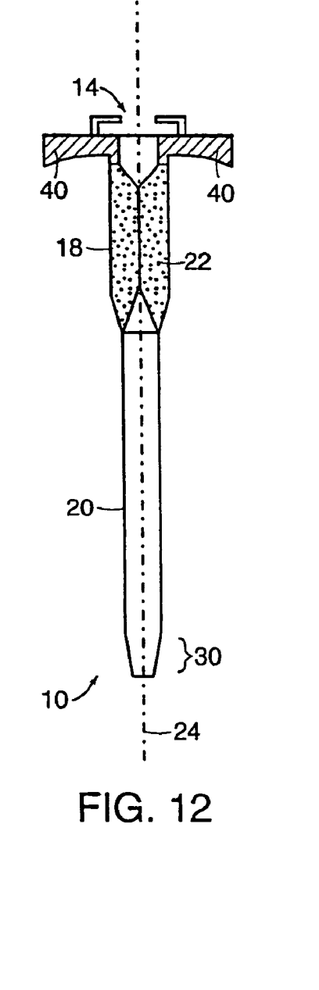
FIG. 12 is a partial sectional view of the sheath of FIG. 10, without the catheter of FIG. 10 inserted into the sheath and thus with the valve of the sheath completely closed along its entire length.

Referring to FIGS. 14 and 10-12, a valved introducer sheath 10 according to the invention includes a body portion 12 and a proximal hub portion 14, with a passageway extending through the entire length of the sheath 10. The hub portion 14 comprises a pair of wings 40 that extend substantially perpendicular to the body portion 12. The passageway is sized to receive a dilator 16 that generally is more rigid than the body portion 12 of the sheath 10. The body portion 12 of the sheath 10 includes at least a first section 18 and a second section 20, where the first section 18 has a larger cross-sectional area than the second section 20, such that the transition 38 from the first section 18 to the second section 20 defines a shoulder or other discontinuity. For example, if the elongated body portion 12 of the sheath 10 is generally circular in cross-section, the first section 18 has a larger diameter than the second section 20. The body portion 12 of the sheath 10 could have non-circular cross-sectional shapes, such as the oblong shape shown in FIG. 9. In an alternative embodiment, the body portion 12 has a single constant cross-sectional area along its entire length. In other embodiments, the body portion 12 can taper (proximal-to-distal, or distal-to-proximal, for example) or otherwise have a varying cross-sectional area along its length. Along and within at least a portion of the passageway (such as some or all of the length of the first section 18), an elongated valve 22 extends longitudinally along the lengthwise axis 24 of the first section 18 and the sheath 10 generally. In the disclosed embodiment, the elongated valve 22 extends along and within the entire length of the first section 18. In this embodiment, the first section is about 2 cm in length and about 0.230 inches in diameter, and the second section is about 14 cm in length and about 0.200 inches in diameter, and thus the elongated valve 22 is approximately 2 cm in length. Also, in this embodiment, the thickness of the wall of the body portion 12 is about 0.010 inches, and can range generally, for example, from about 0.008 inches to about 0.015 inches in thickness.

In the disclosed embodiment, the ratio of the length of the valve 22 to the diameter of the valve 22 is about 3.5, because 2 cm divided by 0.230 inches equals about 3.423. In general, and in accordance with the invention, this ratio for any elongated valve 22 of the invention will be greater than about 2, and preferably greater than about 3. This is in contrast to the length/diameter ratio of known disc-like valves which generally is less than or equal to about 2, and usually less than or equal to about 1. One of ordinary skill will recognize the design trade-offs between the additional sealing capability due to the length of the valve and the additional friction resulting from extending the length of the valve. Depending on the valve material(s), a variety of valve ratios are within the scope of this invention.

This elongated valve 22 of the invention can be formed of a foam material or other compliant material that will allow the dilator 16 to pass therethrough and that will form a seal therearound, but that will also close and form a reliable seal after the dilator 16 is removed. The elongated valve 22 of the invention also will allow a device more flexible than the dilator 16, such as a flexible catheter 36, to be passed therethrough, and it will form a seal around such a device and then close and seal after the device is removed. The larger cross-sectional area of the first section 18 of the body portion 12 of the sheath 10, as compared to the second section 20, provides space for the material (e.g., foam) of the elongated valve 22 to compress and compact when a dilator or other medical device (e.g., the flexible catheter 36) is inserted through the elongated valve 22 and into and through the second section 20 of the body portion 12 of the sheath 10. This extra space in the first section 18 thus allows the elongated valve 22 to open fully and seal around the medical device inserted through the sheath 10, even when the inserted medical device has a diameter (or cross-sectional area) that is equal to, about the same as, or more likely slightly smaller than the inner diameter (or cross-sectional area) of the second section 20 of the body portion 12 of the sheath 10.

Figure 13:
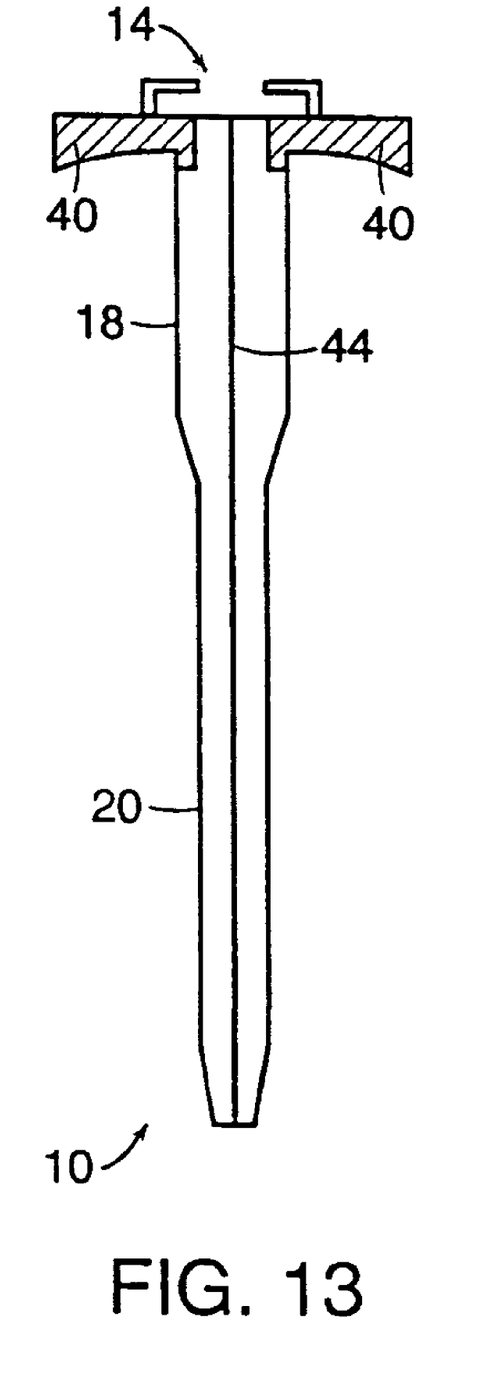
FIG. 13 shows a peelable sheath with scoring or tear lines for separating the sheath.

Referring to FIG. 13, in one embodiment, the valved introducer sheath 10 of the invention is "peelable" in that the body portion 12, hub 14, and valve 22 can be manually broken apart, split, and peeled or separated along scorings or lines 44 that extend at least some of the length and, on opposite sides, of the sheath. The lines or scorings 44 are shown extending the entire length of the sheath 10, but they may instead extend less than the entire length. The sheath can be separated from around the device that extends therethrough (such as the dilator 16 or, more typically, a catheter such as the flexible catheter 36). In another embodiment, the sheath 10 is not peelable. In the peelable embodiment, once peeled from around the inserted device and removed from the body of the patient, the two halves of the now-torn valved introducer sheath 10 are discarded.

Figure 4:
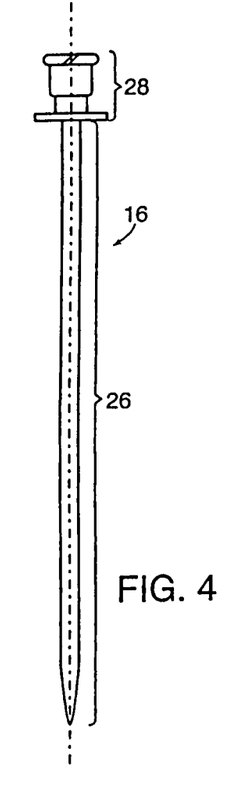
FIG. 4 shows the dilator of FIG. 1 when removed from the sheath of FIG. 1.
Figure 5:
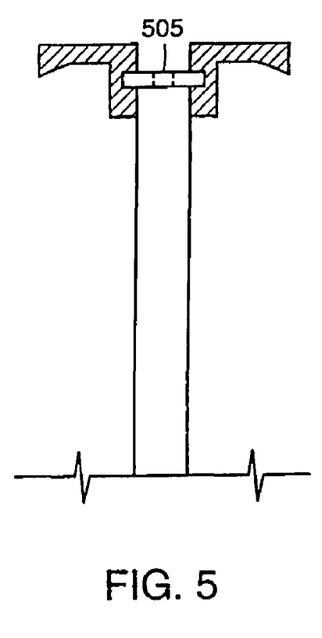
FIG. 5 is a partial sectional view of a conventional valved sheath, with a slit valve.
Figure 6:
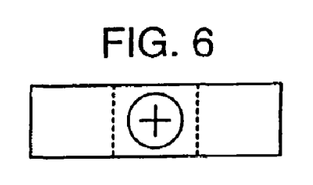
FIG. 6 is a top view of the conventional valved sheath of FIG. 5, showing two cross slits that form the slit valve of the sheath of FIG. 5.
Figure 7:
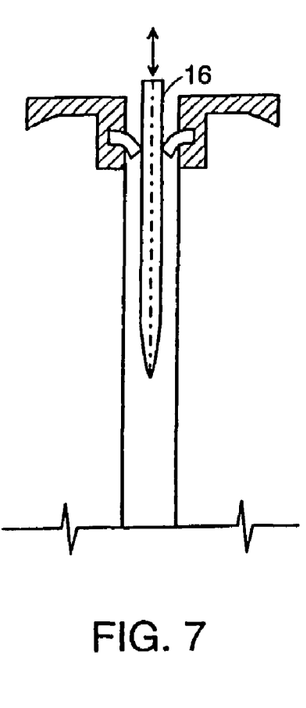
FIG. 7 is a partial sectional view of the conventional valved sheath of FIG. 5, with a dilator passing through the slit valve of the sheath and extending partially into the sheath.
Figure 8:
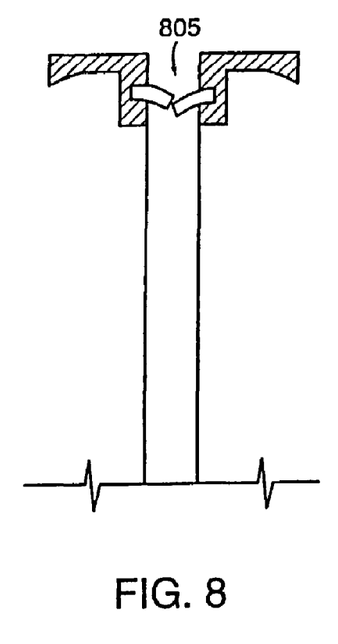
FIG. 8 is a partial sectional view of the conventional valved sheath of FIG. 5, with the dilator of FIG. 7 completely removed from the sheath and the slit valve left in a malpositioned and open state that will allow air influx and/or blood outflow.

The dilator 16 includes a substantially rigid (at least generally more rigid than the body portion 12 of the sheath 10) and elongated portion 26 and a hub portion 28. The hub portion 28 of the dilator 16 is designed to be received by the proximal hub portion 14 of the sheath 10. In the disclosed embodiment, the hub 28 of the dilator 16 can be locked into the hub 14 of the sheath 10 by inserting the elongated portion 26 of the dilator 16 into the sheath 10 and fitting the hub 28 of the dilator 16 and then turning the dilator 16 (or perhaps turning just the hub 28 of the dilator 16) to lock it into the receiving structure on the hub 14 of the sheath 10.

In other embodiments, the hub 26 of the dilator 16 locks to the hub 14 of the sheath 10 in a different fashion, or they do not lock or twist together at all and instead the hub 26 of the dilator 16 just contacts the hub 14 of the sheath 10 when the dilator 16 is fully inserted into the sheath 10.

The valved introducer sheath 10 of the invention, along with the dilator 16, can be used to place the catheter 36 (dr other medical device) into the body of a patient. For example, a large Central Venous Catheter (CVC) can be inserted into a patient's vein with the help of the valved introducer sheath 10. Also, the sheath 10 can be used to help place a dialysis catheter into a patient. During the time in which the dilator 16 is removed from the sheath 10, but prior to insertion of the catheter into the sheath 10, there is a risk that air can be aspirated into the patient's venous system through the sheath, causing major medical complications. Also, when placing a catheter 36 or other device into the body of a patient, there may be a risk that blood or other bodily material or fluid can escape from the patient. In any event, and in general, the valved introducer sheath 10 of the invention can be used to place such medical devices into the body without the risk of substantially anything entering into or escaping from the body. The elongated valve 22 of the invention provides a reliable and effective seal that is easy to manufacture and that will seal properly even after repeatedly being opened and closed by inserting and removing a dilator 16 and/or catheter 36 and/or other medical device through the elongated valve 22.

The elongated valve 22 of the invention will seal before substantially any air or other material can either enter or exit the body of the patient, thereby substantially eliminating and preventing any risk to the patient, such as the risk of air embolism. The elongated valve 22 provides a seal that is more robust than known valves, such as slit valves, because the elongated valve 22 has a large surface area that is oriented along the length of the sheath 10. The elongated valve 22 generally is easier to peel apart than known valves, such as slit valves, because the elongated valve 22 tears in half more easily along its length. Also, the elongated valve 22 is not part of the hub 14 of the sheath 10, and thus the hub 14 of the sheath 10 generally is easy to manufacture and easy to break in half, as compared to conventional valved sheaths that use disc-like slit valves incorporated into the hub of the sheath. It is easier and less expensive to manufacture the hub 14 of the invention (whether it can be peeled apart or not) than it is to make the more-complex hub of a known sheath (whether it can be peeled apart or not) which includes the slit valve as part of the hub assembly.

Figure 1:
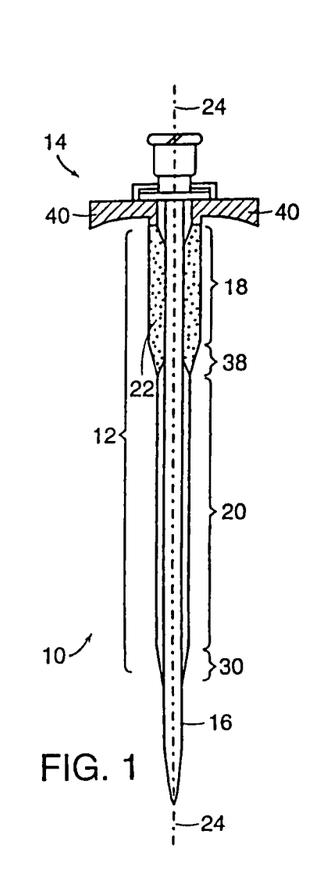
FIG. 1 is a partial sectional view of a valved introducer sheath according to the invention, with a dilator inserted into the sheath and thus with a valve of the sheath open.
Figure 2:
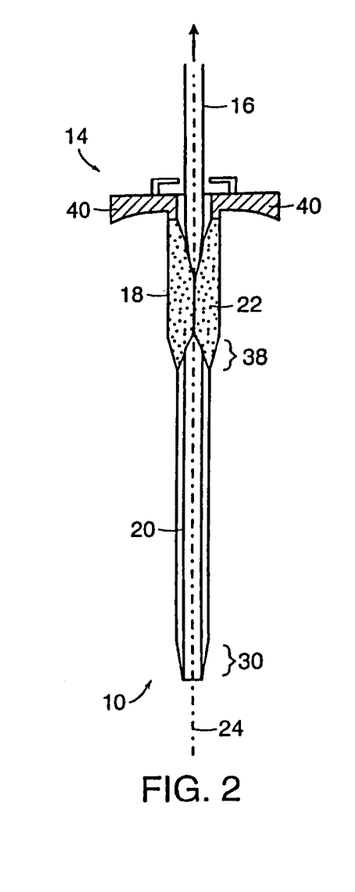
FIG. 2 is a partial sectional view of the sheath of FIG. 1, with the dilator of FIG. 1 partially removed from the sheath and thus with the valve of the sheath closed along a distal part of its length.

The elongated valve 22 of the invention establishes a seal even before the dilator 16, catheter 36, or other medical device is removed from the sheath 10, as illustrated in FIG. 2. Also, the lengthwise structure of the elongated valve 22 provides a high security seal after the dilator 16 or other medical device is removed even if the body portion 12 of the sheath 10 is bent or twisted during the rest of the clinical procedure.

Known slit valves 505 formed into the hub of known valved sheaths, as shown in FIGS. 5-8, can become malpositioned when the dilator 16, catheter 36, or other medical device is removed, even after the first time the dilator 16, catheter 36, or other medical device is inserted and removed. This malpositioning results in a slit valve 505 that is not completely closed upon removal of the dilator 16, catheter 36, or other medical device (FIG. 8), and thus air and/or blood and/or other material can enter and/or exit the body of the patient through the deformed slit valve 805. The conventional slit valve 505 is disc-like and is not extended along the longitudinal length of the sheath 10 or the hub 14, and thus it cannot provide the multitude of benefits provided by the elongated valve 22 of the invention.

The elongated valve 22 of the invention can be formed of a foam material or other material or combination of materials. The elongated valve 22 must allow the dilator 16 or other medical device, such as the catheter 36, to pass therethrough, and it must form a seal therearound. The elongated valve 22 also must close and form a reliable seal after the dilator 16 or other medical device is removed, and it must form a reliable seal even after repeated insertions and removals of dilators 16 and/or catheters 36 and/or other devices. If a foam material is selected as the material to be used to form the elongated valve 22, the foam material should be very light (i.e., its volume should be largely occupied by gas) to minimize resistance to passage during the insertion and removal of dilators, catheters, and other devices. Also, the foam material selected should be very elastic in that it consistently springs closed when the devices (e.g., dilators, catheters, etc.) are removed. The foam material should be closed cell to minimize absorption of fluids (i.e., liquids or gasses). The foam material also should be tough in that it does not wear, degrade, or generate debris (for example, pieces should not break off) as a result of friction associated with devices being inserted into and removed from the valve 22. The foam material used to form the valve 22 could be lubricated to minimize friction. The foam material could be carried in a solvent which enables it to adhere to the inner walls of the first section 18 of the body portion 12 of the sheath 10, and the foam material should be bio-compatible and capable of being sterilized. Some foam materials that possibly could be used, as long as they meet all or most of the above-identified requirements, include silicones, polyurethanes, polyethylenes, and the like.

The body portion 12 of the sheath 10, which can be extruded to form its shape, can be made from any of a variety of materials or combination of materials. The body portion 12 can be made, for example, of polyethylene or other thermoformable plastic, and such a material would allow the body portion 12 of the sheath 10 to be set into a curved or bent configuration rather than the depicted straight geometry. In some applications, such as accessing the left internal jugular vein, a pre-curved or pre-bent body portion 12 of the sheath 10 would have clinical advantages including ease of placing and lack of kinking which might happen if one were to bend a straight sheath. If the body portion 12 of the sheath 10 were made from a thermoset Teflon type material, which it could be, it generally would not be able to be pre-curved or pre-bent and likely would have to be provided straight.

Figure 14:
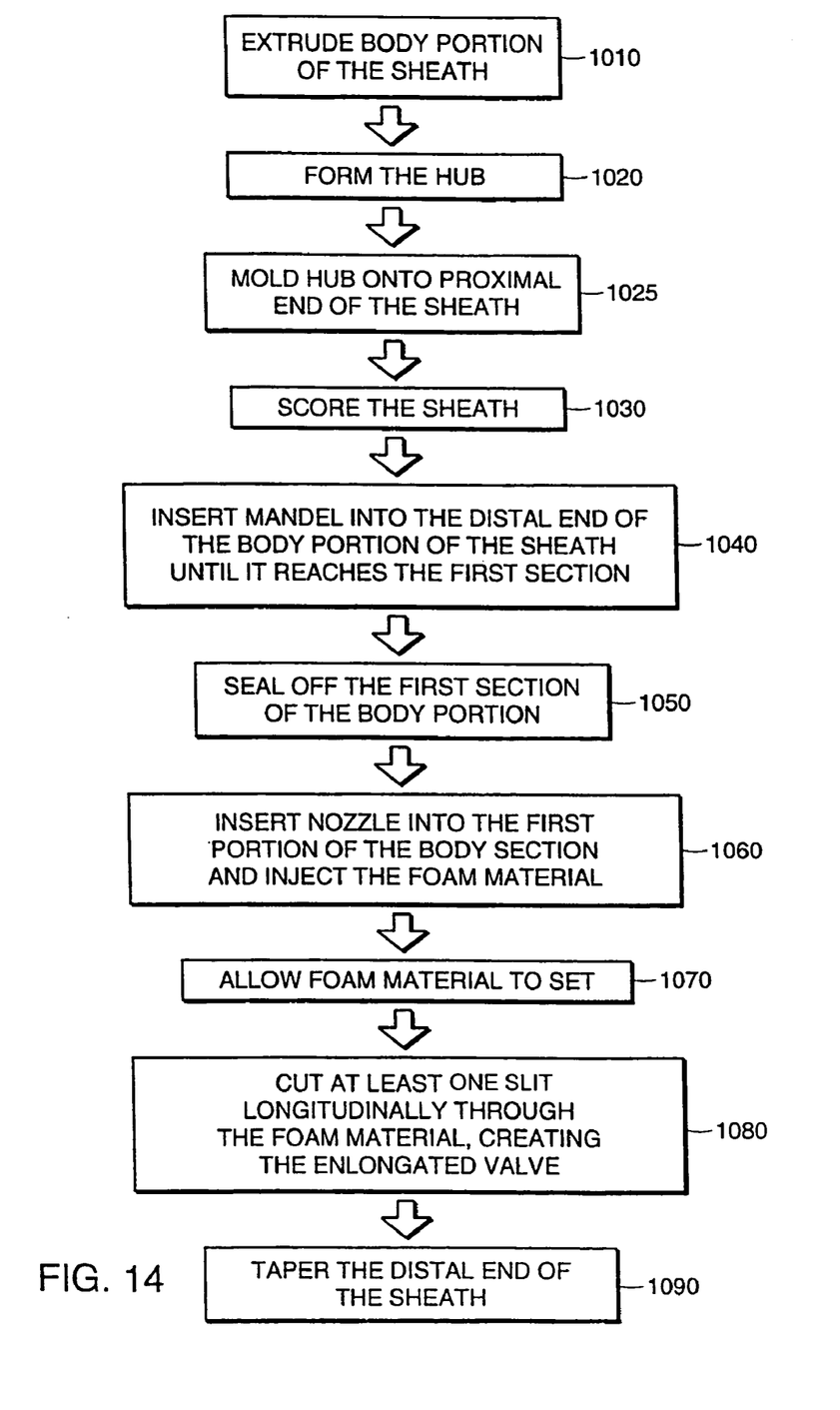
FIG. 14 is a flow diagram illustrating a method of making a valved introducer sheath according to one embodiment of the invention.
Figure 15:
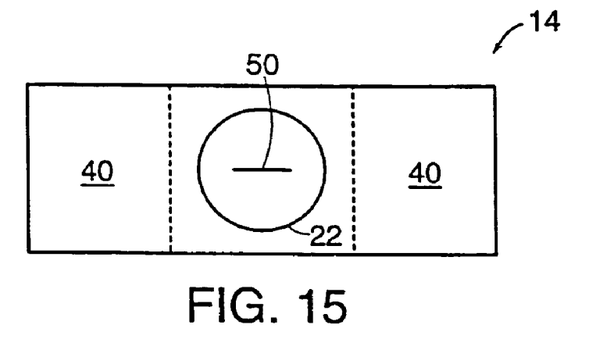
FIG. 15 is a top view, along the longitudinal axis of the sheath, of an elongated valve comprising one slit according to one embodiment of the invention.

Referring to FIG. 14, one possible method of manufacturing the valved introducer sheath 10 of the invention would include the following steps.

First, the body portion 12 of the sheath 10 is extruded (Step 1010). The hub 14 of the sheath 10 also is formed (Step 1020), and then the hub 14 is molded onto the proximal end of the sheath 10 (i.e., the proximal end of the first section 18 of the body portion 12 of the sheath 10) (Step 1025), as shown in FIGS. 1-3 and 10-12.

The body portion 12 of the sheath 10 then can be scored to allow the sheath 10 to be peeled into two halves (Step 1030). Alternatively, if the material(s) from which the body portion 12 is formed is/are "highly oriented," there possibly would be no need to score the length of the body portion 12 as such material(s) would tend to peel apart naturally into two halves. If the sheath 10 is not to be peelable, it would not be necessary to perform the scoring step or to select a highly oriented material.

A mandrel can then be inserted into the distal end 30 of the body portion 12 of the sheath 10 until it enters the first section 18 (which is larger than the second section 20 of the body portion 12 of the sheath 10) or until it reaches the transition point between the first and second sections 18, 20 (Step 1040). The mandrel is then adjusted so that it provides a seal between itself and the inner wall of the second section 20 of the body portion 12—the mandrel can be equipped with a balloon which can be inflated to contact the inner wall of the second section 20 near or at the transition point between the first and second sections 18, 20, for example. Regardless of whether the mandrel or some other mechanism is used, the point is to seal off a section of the body portion 12 (Step 1050) so that the foam can be placed in the first section 18 to form the elongated valve 22.

Figure 3:
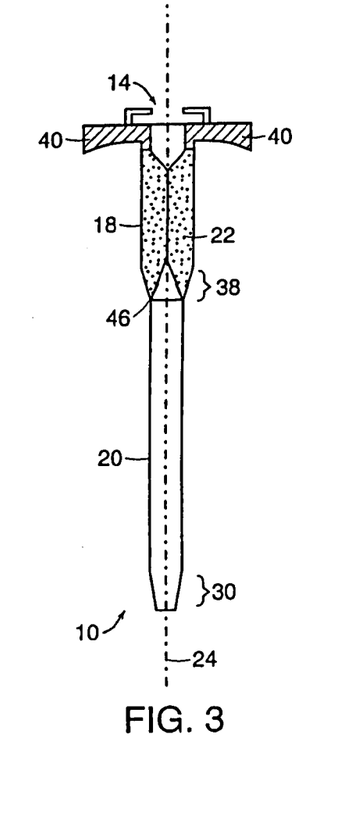
FIG. 3 is a partial sectional view of the sheath of FIG. 1, without the dilator of FIG. 1 inserted into the sheath and thus with the valve of the sheath completely closed along its entire length.

A nozzle can now be inserted into the proximal end of the sheath 10 through the hub 14 and into the first section 18 of the body portion 12, and liquid foam material (e.g., a polyurethane material) can be injected into the first section 18 of the body portion 12 of the sheath 10 (Step 1060). The foam material should be allowed to set and to adhere to the inner wall of the first section 18 (Step 1070). If necessary to set (or better set) the foam material and/or to cause it to adhere (or better adhere) to the inner wall of the first section 18 of the body portion 12 of the sheath 10, heat can be applied for an appropriate amount of time and at an appropriate temperature or temperatures. During the time the foam material is allowed to set and adhere to the inner wall of the first section 18, the nozzle used to inject the foam material into first section 18 of the body portion 12 of the sheath 10 may remain inserted into the first section 18 of the body portion 12 in order create a conical or other shaped depression in the proximal end of foam material. Referring to FIG. 3, the mandrel that is used to seal off the second section 20 from the first section 18 can also be used to create a conical or other shaped depression in the distal end of the foam material. This depression facilitates easy advancement of the sheath 10 over a flexible medical device, such as a hubless catheter, that is inserted into the sheath 10 at the distal end. Alternatively, at least the distal end of the foam material can be formed without any type of shaped depression, and can instead be flat, as indicated by the short horizontal dotted line 46. The shaped (e.g., conical) depression in the proximal end of the foam material can be used to guide easily various medical devices into the one or more slits. This depression facilitates easy entry of a flexible medical device, such as the catheter 36, into the elongated valve 22.

Once properly set and adhered, a scalpel type device is used to create at least one slice or slit 50 (FIGS. 15-18) longitudinally through the center of the foam material while leaving the block of foam in place, thereby creating the elongated valve 22 (Step 1080). If the sheath 10 is peelable, at least one slit 50 should be oriented to coincide with the scoring, or the natural tear line 44, of the body portion 12 of the sheath 10 to allow the elongated valve 22, the body portion 12, and the hub 14 to separate into two halves easily, neatly, and evenly (which can be formed as described below).

The very distal end of the body portion 12 of the sheath 10 could then be tapered appropriately (Step 1090). As seen in FIGS. 1-3 and 10-12, the distal end 30 of the body portion 12 of the sheath 10 is tapered, and this generally helps reduce any abrupt transitions between the end of the body portion 12 and the dilator 16, catheter 36, or other medical device that extends therefrom, to allow the entire assembly to slide more easily into the body of the patient (over a guide wire, typically). Step 1090 is performed last to prevent potential damage to the distal end 30 from the insertion of the mandrel (Step 1040). However, step 1090 could be executed earlier.

Figure 16:
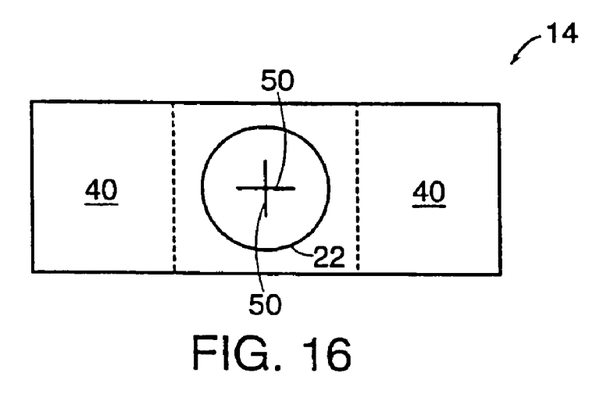
FIG. 16 is a top view, along the longitudinal axis of the sheath, of an elongated valve comprising two slits according to one embodiment of the invention.
Figure 17:
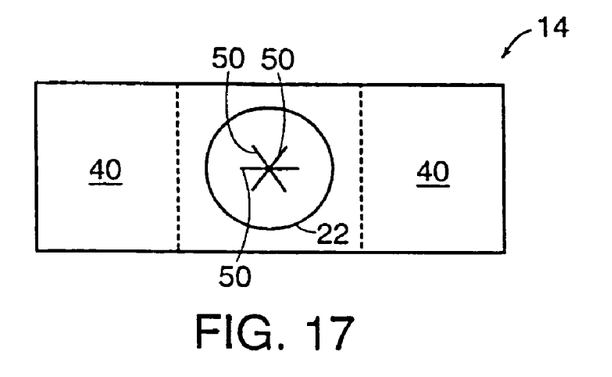
FIG. 17 is a top view, along the longitudinal axis of the sheath, of an elongated valve comprising three slits according to one embodiment of the invention.

Referring to FIG. 16, whether the sheath 10 is peelable or not, one embodiment of the elongated valve 22 is formed by two slits 50 that cross each other and are oriented ninety degrees with respect to each other to form an "X" or "+" configuration when viewed straight down from the top of the sheath 10 along the longitudinal axis of the sheath 10 and the elongated valve 22. Elongated valves of the invention can be formed with one or more longitudinal slits 50 oriented in a variety of configurations. For example, one (FIG. 15), two (FIG. 16, 18), three (FIG. 17), or more slits 50 can be used to form the elongated valve 22.

Figure 18:
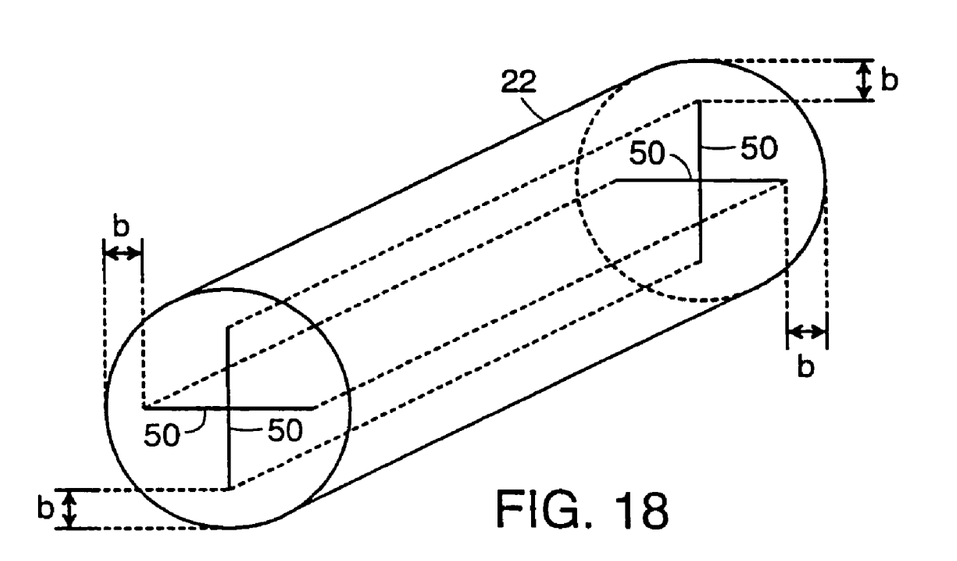
FIG. 18 is a three-dimensional perspective view of an elongated valve comprising two slits according to one embodiment of the invention.

Referring to FIG. 18, none of the one or more slits 50 in the foam material extend in width to the inner wall of the sheath. That is, there is an unbroken "band" of foam material on the edge of valve 22 along its entire length, as indicated by the distance "b" in FIG. 18.

Still referring to FIG. 18, the valve 22, if it could be removed in one piece from the body portion 12 of the sheath 10 (which it cannot, because it is affixed or adhered to at least a portion of the inner surface to the sheath 10 that defines the passageway through the sheath 10), would have the same shape it has when in place within the sheath 10. The removed valve 22 would not expand, as it is not held in a compressed state within the sheath 10, as with some inserts that are used in known sheaths. The removed valve 22 would retain the shape and configuration it has when it is in the sheath 10, with the slit(s) 50 of the valve 22 closed when nothing is inserted into the slit(s) 50.

Elongated valves (22) in accordance with the invention could be used in other types of medical devices instead of the introducer sheath 10 described herein. In general, any type of medical device requiring valving could benefit from the use of an elongated valve 22 of the type described herein. Elongated valves 22 of the invention eliminate or at least minimize the undesired transfer of fluids and/or gasses, and such elongated valves 22 could be useful in a variety of medical procedures when incorporated into any of a variety of different medical devices.

Variations, modifications, and other implementations of what is described herein will occur to those of ordinary skill in the art without departing from the spirit and the scope of the invention. Accordingly, the invention is not to be defined solely by the preceding illustrative description.

What is claimed is:

1. A method of producing a valved sheath, comprising:
   (a) providing a sheath comprising a proximal hub portion, an elongated body portion extending distally from the proximal hub portion, and a passageway extending through the proximal hub and elongated body portions;
   (b) injecting a foam material into at least some of the passageway; and
   (c) forming in the foam material one or more self-sealing slits, the foam material and the one or more slits serving as a valve in the passageway of the sheath.

2. The method of claim 1 wherein step (b) comprises injecting the foam material such that the length of the foam material within the passageway is greater than the width of the foam material at any point within the passageway.

3. The method of claim 1 wherein step (c) comprises forming the one or more self-sealing slits such that none of the one or more self-sealing slits extends in width to an inner surface of the sheath that defines the passageway.

4. The method of claim 1 wherein step (c) comprises forming the one or more self-sealing slits such that the one or more self-sealing slits substantially prevent the flow of gas into the passageway of the sheath.

5. The method of claim 1 further comprising providing a pair of lines extending at least some of the length, and on opposite sides, of the sheath, the sheath being separable along the lines.

6. The method of claim 1 further comprising scoring the sheath along at least some of its length.

7. The method of claim 6 wherein the scoring comprises scoring a pair of lines that extend at least some of the length, and on opposite sides, of the sheath, the sheath being separable along the lines.

8. The method of claim 1 wherein step (a) comprises providing the sheath comprising the proximal hub portion which comprises a pair of wings extending substantially perpendicular to the elongated body portion of the sheath.

9. The method of claim 1 wherein step (b) comprises injecting the foam material which comprises a closed cell foam.

10. The method of claim 1 wherein step (b) comprises injecting the foam material such that the foam material becomes affixed to a portion of an inner surface of the sheath that defines the passageway.

* * * * *